(12) United States Patent
Yomtov et al.

(10) Patent No.: US 12,402,827 B2
(45) Date of Patent: Sep. 2, 2025

(54) METHODS OF VENTRICULAR ARRHYTHMIA LOCALIZATION USING A 3D HEART MODEL

(71) Applicant: KardioNav, Inc., Mt. Olive, NJ (US)

(72) Inventors: Barry Yomtov, Marblehead, MA (US); Tracy K. Ginnings, Salem, VA (US)

(73) Assignee: KardioNav, Inc., Fort Mills (SC)

( * ) Notice: Subject to any disclaimer, the term of this patent is extended or adjusted under 35 U.S.C. 154(b) by 356 days.

(21) Appl. No.: 17/372,470

(22) Filed: Jul. 11, 2021

(65) Prior Publication Data

US 2022/0007990 A1    Jan. 13, 2022

Related U.S. Application Data

(60) Provisional application No. 63/050,542, filed on Jul. 10, 2020.

(51) Int. Cl.
| | |
|---|---|
| A61B 5/367 | (2021.01) |
| A61B 5/055 | (2006.01) |
| A61B 5/28 | (2021.01) |
| A61B 5/339 | (2021.01) |

(52) U.S. Cl.
CPC .............. *A61B 5/367* (2021.01); *A61B 5/055* (2013.01); *A61B 5/28* (2021.01); *A61B 5/339* (2021.01)

(58) Field of Classification Search
CPC ................................. A61B 5/367; A61B 5/339
USPC ........................................................ 600/515
See application file for complete search history.

(56) References Cited

U.S. PATENT DOCUMENTS

| | | |
|---|---|---|
| 5,657,755 A | 8/1997 | Desai |
| 5,687,737 A | 11/1997 | Branham et al. |
| 7,787,951 B1 | 8/2010 | Min |
| 8,155,739 B2 | 4/2012 | Keel et al. |
| 8,326,419 B2 | 12/2012 | Rosenberg et al. |
| 8,478,388 B2 | 7/2013 | Nguyen et al. |
| 8,615,298 B2 | 12/2013 | Ghosh et al. |
| 9,078,573 B2 | 7/2015 | Ramanathan et al. |
| 9,155,897 B2 | 10/2015 | Ghosh et al. |

(Continued)

FOREIGN PATENT DOCUMENTS

| | | |
|---|---|---|
| CN | 101828915 A | 9/2010 |
| WO | 2009/129475 A1 | 10/2009 |

(Continued)

OTHER PUBLICATIONS

International Search Report and Written Opinion for counterpart Application No. PCT/US2019/043900, dated Nov. 20, 2019.

(Continued)

*Primary Examiner* — Nicole F Johnson
(74) *Attorney, Agent, or Firm* — The Marbury Law Group, PLLC

(57) ABSTRACT

A method of arrhythmia localization and model merging includes: generating a three-dimensional (3D) heart model of a heart of a patient, the 3D heart model including myocardium wall thickness measurements of the heart; generating an activation map of the heart based on electrocardiogram (ECG) data recorded during premature ventricular contraction (PVC) of the heart, the activation map including a PVC onset point; modifying the 3D heart model to include the PVC onset point; and displaying the modified 3D heart model on a display device.

7 Claims, 8 Drawing Sheets

(56) References Cited

U.S. PATENT DOCUMENTS

| | | | |
|---|---|---|---|
| 9,265,951 B2 | 2/2016 | Sweeney | |
| 9,278,219 B2 | 3/2016 | Ghosh | |
| 9,381,363 B2 | 7/2016 | Ryu et al. | |
| 9,439,578 B2 | 9/2016 | Thakur et al. | |
| 9,510,763 B2 | 12/2016 | Ghosh et al. | |
| 9,579,064 B2 | 2/2017 | Kovtun et al. | |
| 9,586,052 B2 | 3/2017 | Gillberg et al. | |
| 9,681,817 B2 | 6/2017 | Maskara et al. | |
| 9,875,544 B2 | 1/2018 | Rai et al. | |
| 9,877,789 B2 | 1/2018 | Ghosh | |
| 9,986,928 B2 | 6/2018 | Gillberg et al. | |
| 10,016,145 B2 | 7/2018 | Thakur et al. | |
| 10,369,358 B2 | 8/2019 | Monteiro | |
| 10,471,263 B2 | 11/2019 | Pacheco | |
| 10,713,790 B2 | 7/2020 | Adler | |
| 10,932,863 B2 | 3/2021 | Adler | |
| 2009/0099679 A1 | 4/2009 | Sandoval et al. | |
| 2009/0287087 A1 | 11/2009 | Gwerder et al. | |
| 2010/0268059 A1 | 10/2010 | Ryu et al. | |
| 2011/0071583 A1 | 3/2011 | Muntendam | |
| 2012/0157822 A1 | 6/2012 | van Dam et al. | |
| 2013/0116533 A1 | 5/2013 | Lian et al. | |
| 2013/0116681 A1 | 5/2013 | Zhang | |
| 2013/0310890 A1 | 11/2013 | Sweeney | |
| 2014/0107510 A1 | 4/2014 | Bogun et al. | |
| 2014/0194760 A1 | 7/2014 | Albert | |
| 2016/0249880 A1 | 9/2016 | Konofagou et al. | |
| 2016/0331261 A1 | 11/2016 | Someya et al. | |
| 2016/0342761 A1 | 11/2016 | Whiting et al. | |
| 2016/0345833 A1 | 12/2016 | Adams | |
| 2017/0011197 A1 | 1/2017 | van Dam et al. | |
| 2017/0071492 A1 | 3/2017 | van Dam et al. | |
| 2017/0178403 A1 | 6/2017 | Krummen et al. | |
| 2018/0064947 A1 | 3/2018 | Pacheco et al. | |
| 2018/0303345 A1* | 10/2018 | Adler | A61B 6/5247 |
| 2019/0038357 A1 | 2/2019 | Adler | |
| 2019/0053728 A1* | 2/2019 | Yang | A61B 5/0044 |
| 2019/0060006 A1 | 2/2019 | Van Dam et al. | |
| 2019/0111265 A1 | 4/2019 | Zhou | |
| 2020/0029817 A1 | 1/2020 | Adler | |
| 2020/0061383 A1 | 2/2020 | Yomtov et al. | |

FOREIGN PATENT DOCUMENTS

| | | |
|---|---|---|
| WO | 2012/061612 A2 | 5/2012 |
| WO | 2013/006713 A2 | 1/2013 |
| WO | 2015/170978 A1 | 11/2015 |

OTHER PUBLICATIONS

International Preliminary Report on Patentability for counterpart Application No. PCT/US2019/043900, dated Feb. 11, 2021.
International Search Report and Written Opinion for counterpart Application No. PCT/US2017/050188, dated Nov. 7, 2017.
International Preliminary Report on Patentability for counterpart Application No. PCT/US2017/050188, dated Mar. 21, 2019.
International Search Report and Written Opinion for counterpart Application No. PCT/US2018/044746, dated Jan. 28, 2019.
International Preliminary Report on Patentability for counterpart Application No. PCT/US2018/044746, dated Feb. 13, 2020.
Invitation to Pay Additional Fees from EP for counterpart Application No. PCT/US2018/044746, dated Nov. 14, 2018.
International Search Report and Written Opinion for counterpart Application No. PCT/US2020/045764, dated Nov. 17, 2020.
Daubert, C., et al., "Avoiding non-responders to cardiac resynchronization therapy: a practical guide," European Heart Journal Advance Access, European Heart Journal, doi: 10.1093/eurheart/ehw270, published Jul. 1, 2016.
Ploux, Sylvain MD, et al., "Noninvasive Electrocardiogramapping to Improve Patient Selection for Cardiac Resynchronization Therapy," Journal of Americal College of Cardiology, vol. 61, No. 24, ISSN 0735-1097/$36.00, 2013, pp. 2435-2443.
Noheria, et al., "Ablating Premature Ventricular Complexes: Justification, Techniques, and Outcomes," MDCVJ | XI (2), houstonmethodist.org/debakey-journal, 2015, pp. 109-120.
Schulze, Walther et al., "Automatic camera-based identification and 3-D reconstruction of electrode positions in electrocardiographic imaging," Biomed. Eng.-Biomed. Tech. 59(6): 2014, pp. 515-528.
Van Dam, Peter, et al., "New Computer Program for detecting 12 Lead ECG Misplacement using a 3D Kinect Camera," Computing in Cardiology, 40, ISSN 2325-8861, 2013, pp. 1175-1178.
Vijayaraman, Pugazhendhi Dr., et al., "His-Optimized Cardiac Resynchronization Therapy to Maximize Electrical Resynchronization a Feasibility Study," Circ Arrhythm Electrophysiol, Feb. 2019, 12:e006934. DOI: 10.1161/CIRCEP.118.006934, pp. 1-9.
Padeletti, Luigi MD., et al., "Simultaneous His Bundle and Left Ventricular Pacing for Optimal Cardiac Resynchronization Therapy Delivery Acute Hemodynamic Assessment by Pressure-Volume Loops," Circ Arrhythm Electrophysiol. 2016;9:e003793. DOI: 10.1161/CIRCEP.115.003793, pp. 1-8 (downloaded from http://ahajournals.org on Nov. 18, 2020).
Copending U.S. Appl. No. 17/174,328, Inventor: Barry Yomtov, Title: "Method of Providing Ventricular Arhythmia Localization with a Heart Model Derived from Machine Learning," filed Feb. 11, 2021.
Non-Final Office Action received in copending U.S. Appl. No. 17/174,308 dated Sep. 12, 2023.
Copending U.S. Appl. No. 17/174,308, Inventor: Barry Yomtov, Title: Method of Providing Ventricular Arrhythmia Localization and Myocardium Wall Thickness Within a 3D Heart Model filed Feb. 11, 2021.
Copending U.S. Appl. No. 17/346,074, Inventor: David Jenkins, Title: Methods and Apparatus for Determining Likely Outcomes of an Electrophysiology Procedure filed Jun. 11, 2021.

* cited by examiner

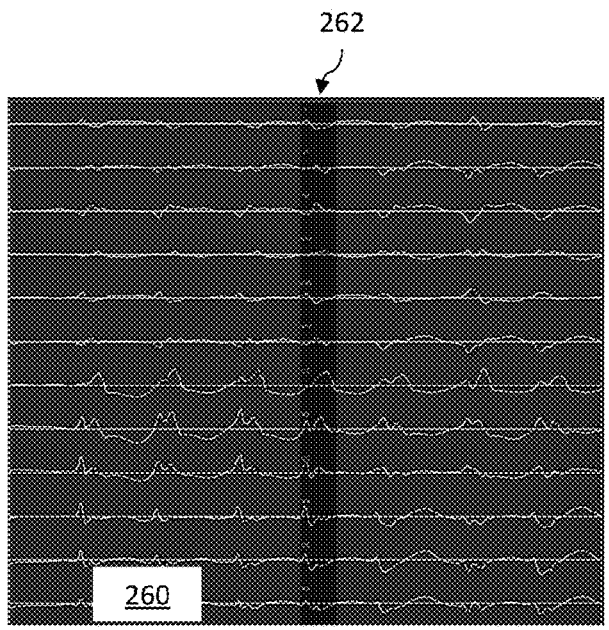# 
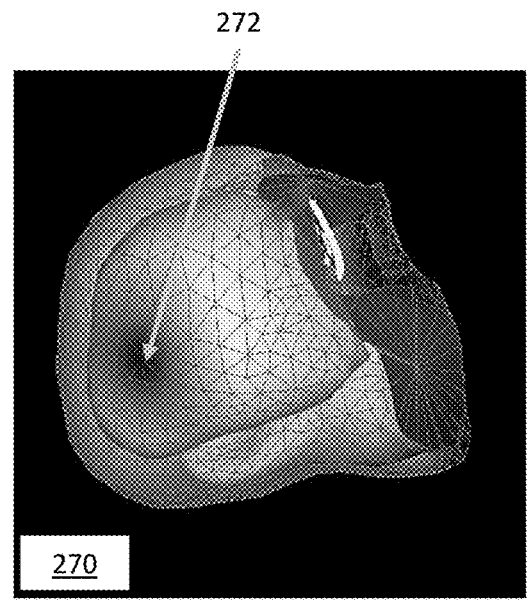
FIG. 9C
FIG. 9D
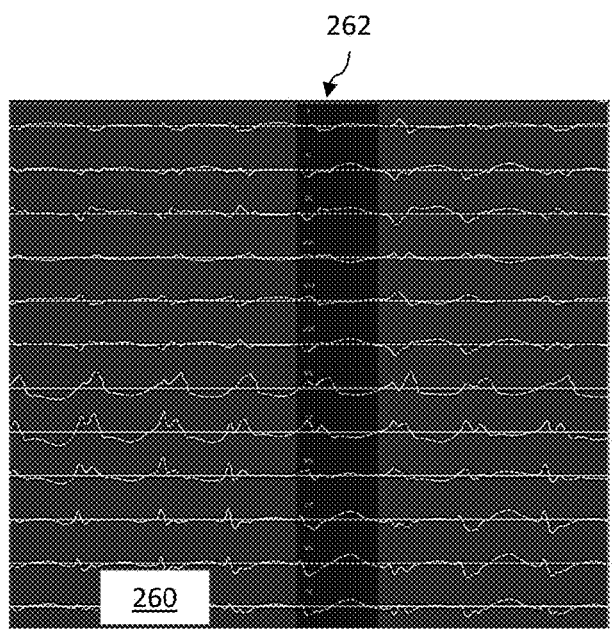
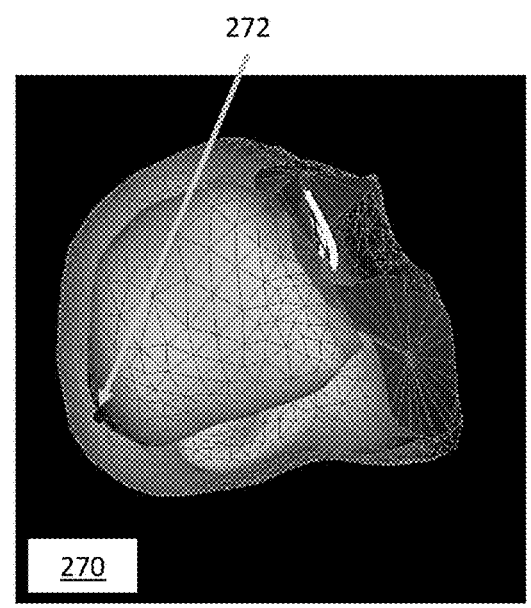
FIG. 9E
FIG. 9F

METHODS OF VENTRICULAR ARRHYTHMIA LOCALIZATION USING A 3D HEART MODEL

RELATED APPLICATIONS

This application claims the benefit of priority to U.S. Provisional Patent Application No. 63/050,542, entitle Methods of Ventricular Arrhythmia Localization Using a 3D Heart Model filed Jul. 10, 2020, the entire contents of which are incorporated herein by reference for all purposes.

BACKGROUND

Heart defects in the cardiac conduction system can result in asynchronous contraction (arrhythmia) of the heart and are sometimes referred to as conduction disorders. As a result, the heart does not pump effectively, which may ultimately lead to heart failure. Conduction disorders can have a variety of causes, including age, heart (muscle) damage, medications and genetics.

Premature ventricular contractions (PVCs) are abnormal or aberrant heart beats that start somewhere in the ventricles rather than in the upper chambers of the heart as with normal sinus beats. PVCs typically result in a lower cardiac output as the ventricles contract before they have had a chance to completely fill with blood. PVCs may also trigger ventricular tachycardia (VT or V-Tach).

VT is another heart arrhythmia disorder caused by abnormal electrical signals in the ventricles of the heart. In VT, the abnormal electrical signals cause the heart to beat faster than normal, usually more than 100 beats per minute, with the beats originating in the ventricles. VT can occur in patients with structurally normal hearts caused by triggered or focal electrical activity. VT can also occur in patients with heart conditions such as myocardial scar caused by myocardial infarction and present as a re-entrant VT.

One common location for idiopathic VT, (not myocardial scar related) is in the right ventricular outflow tract (RVOT), which is the route the blood flows from the right ventricle to the lungs. In patients who have had a heart attack, scarring from the heart attack can create a milieu of intact heart muscle and a scar that predisposes patients to develop VT.

SUMMARY

Various embodiments provide a method of arrhythmia localization and model merging including: generating a three-dimensional (3D) heart model of a heart of a patient, the 3D heart model including myocardium wall thickness measurements of the heart; generating an activation map of the heart based on electrocardiogram (ECG) data recorded during premature ventricular contraction (PVC) of the heart, the activation map including a PVC onset point; modifying the 3D heart model to include the PVC onset point; and displaying the modified 3D heart model on a display device.

Various embodiments provide a method of arrhythmia localization and model merging, including: generating a three-dimensional (3D) heart model of a heart of a patient, the 3D heart model including myocardium wall thickness measurements of the heart; generating an activation map of the heart based on electrocardiogram (ECG) data recorded during ventricular tachycardia (VT) of the heart, the activation map comprising one or more VT exit points; modifying the 3D heart model to include the one or more VT exit points; and displaying the modified 3D heart model on a display device.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

FIGS. 9A-9F are screen shots showing a VT rhythm and corresponding modified 3D heart models, as successive localization points are displayed according to various embodiments.

DETAILED DESCRIPTION

Various embodiments will be described in detail with reference to the accompanying drawings. Wherever possible, the same reference numbers will be used throughout the drawings to refer to the same or like parts. References made to particular examples and embodiments are for illustrative purposes, and are not intended to limit the scope of the claims.

Catheter ablation is the treatment of choice in patients with VT and/or symptomatic PVCs. The targets for ablation are locations in the heart where the PVCs or VT's are occurring. In the case of an idiopathic VT the ablation site would be an arrhythmogenic foci. For scar related tachycardias, the VT would originate from an isthmus and the re-entrant loop would move (enter and exit) through the scar tissue. In order to determine a proper ablation location, a treating physician may first stimulate or pace map in a proposed location, to determine whether the location is close to the isthmus of the VT.

If a desired activation pattern is not achieved when the heart is stimulated at a given location, a new location may be chosen and sampled. Current clinical resources are not able to direct the physician to a more accurate location. Accordingly, there is a need for improved guidance in determining the proper location to stimulate and ultimately ablate the ventricular arrhythmia An electrocardiogram (ECG) is defined herein as any method that (preferably non-invasively) correlates actual electrical activity of the heart muscle to measured or derived (electrical activity) of the heart. In the case of a classical electrocardiogram, the differences in potential between electrodes on the body surface are correlated to the electrical activity of the heart. In order to obtain such a functional image, an estimation of the movement of the electrical activity has to be provided.

Figure 1:
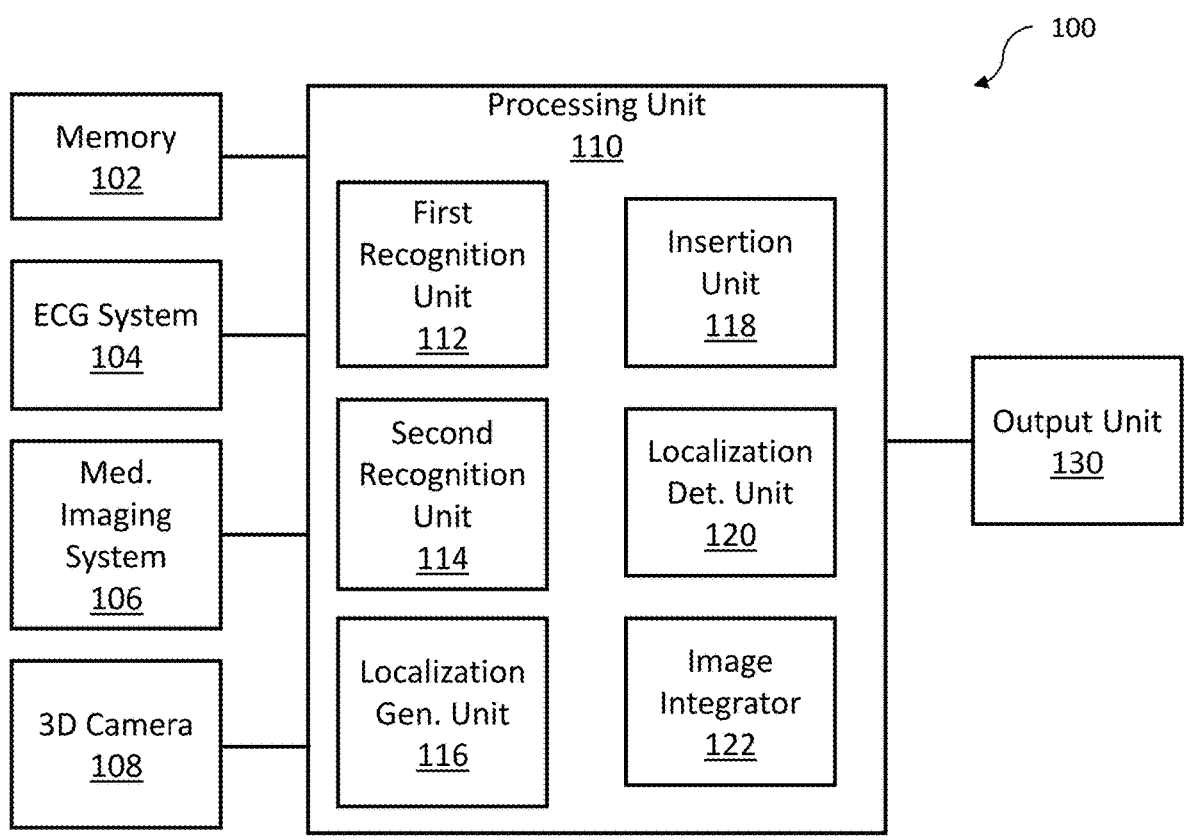
FIG. 1 is a schematic representation of a cardiac mapping system, according to various embodiments.
Figure 2A:
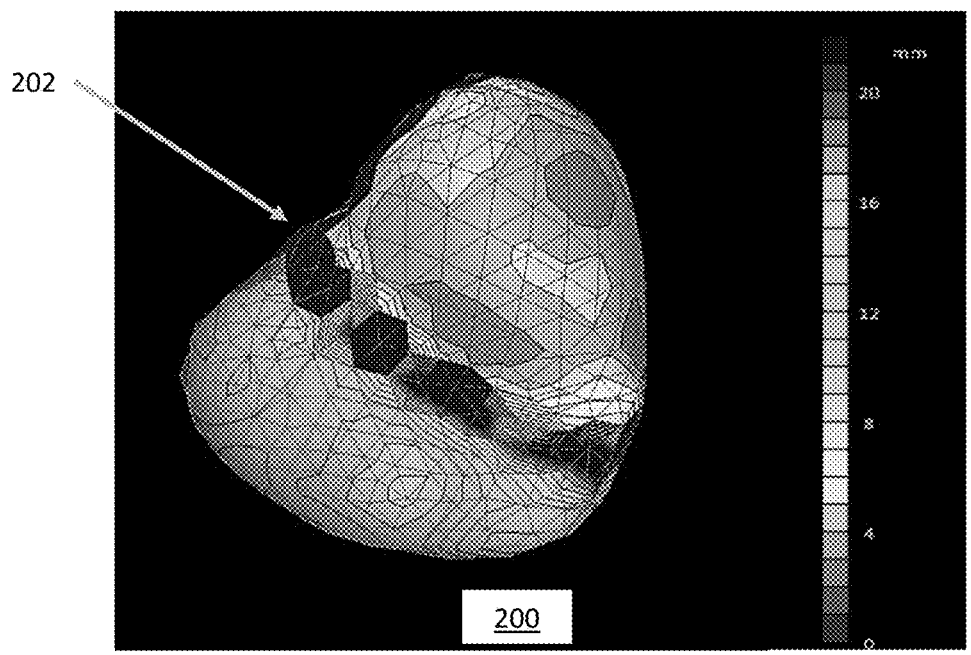
FIG. 2A shows a three-dimensional (3D) heart model that may be generated by the system of FIG. 1.
Figure 2B:
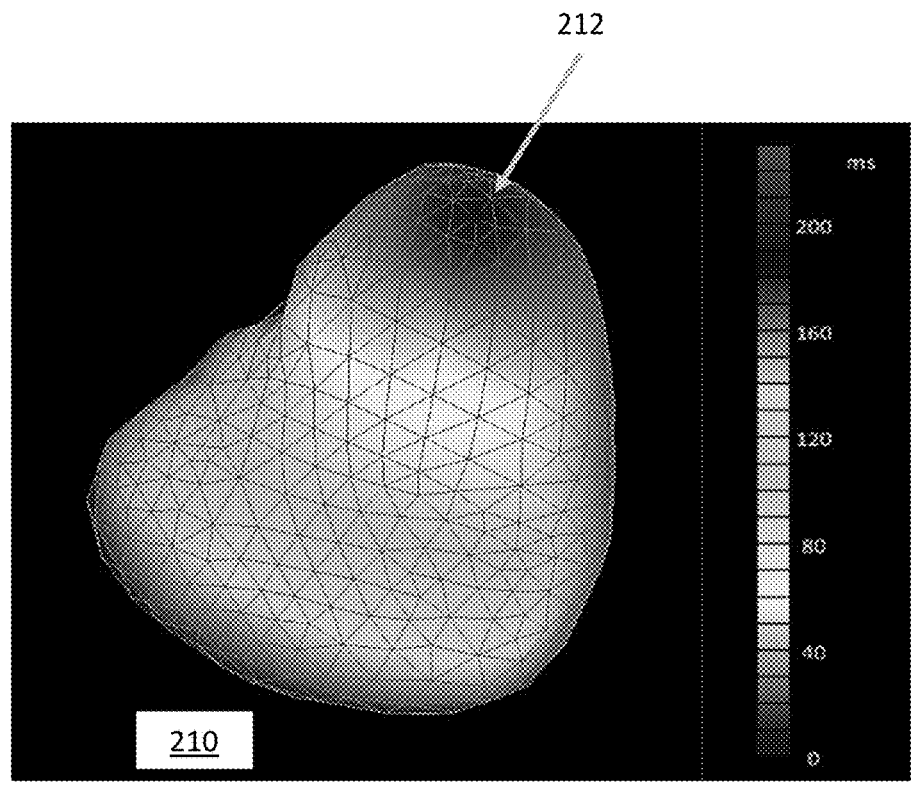
FIG. 2B shows a 3D cardiac activation map that may be generated by the system of FIG. 1.

FIG. 1 is a schematic representation of a cardiac mapping system 100, according to various embodiments of the present disclosure. FIG. 2A shows a three-dimensional (3D) heart model 200 that may be generated by the system 100 of FIG. 1. FIG. 2B shows a 3D cardiac activation map 210 that may be generated by the system 100 of FIG. 1.

Referring to FIGS. 1, 2A, and 2B, the system 100 may include a processing unit 110, a memory 102, and an optional output unit 130. The memory 102 may be configured to store computer-readable data and instructions. The output unit 130 may be a monitor or other display device. The processing unit 110 may include a central processing unit (CPU) or similar integrated circuit device, configured to execute instructions stored in the memory 102 or within the processing unit 110. The processing unit 110 may include a first recognition unit 112, a second recognition unit 114, a localization point generation unit 116, an insertion unit 118, a localization detection unit 120, and an image integrator 122.

The processing unit 110 may be configured to receive patient data from various sources, such as an electrocardiographic (ECG) system 104, a medical imaging system 106, and/or a three-dimensional (3D) camera 108, and may be configured to store such data in the memory 102.

The processing unit 110 may be configured to generate the 3D heart model 200 using patient-specific data generated by the medical imaging system 106. For example, the medical imaging system 106 may be a magnetic resonance image (MRI) device, a computed tomography (CT) device, or the like.

Alternatively or additionally, a 3D anatomical heart model having the closest conformity to the patient's heart may be selected from a database including a plurality of 3D anatomical models. In some embodiments, the heart model may be optionally modified to include patient-specific features. The selected and optionally modified 3D anatomical heart model may serve as the patient-specific 3D heart model 200. Such a model may include detailed structures of the heart such as the aortic cusps, aortic root, aorta, aortic arch, coronary vascular structures, or the like.

For example, the 3D heart model 200 of FIG. 2A may be based on CT scans of the patient. This patient specific 3D heart model 200 may be generated by comparing the patient's digital imaging and communications in medicine (DICOM) standard images to reference heart models obtained from a database of such models that may be stored in local memory or remote memory accessible via a network. The best fitting reference heart model may be selected from the database and then adjusted (e.g., edited) to match to the patient's DICOM images. The edited patient-specific heart model may display the myocardial thickness of the patient's heart. For example, the 3D heart model 200 may include a color-coding scale to represent the myocardium thickness in millimeters. For example, red, orange and yellow colors represent thinner myocardium and green to blue colors may represent thicker myocardium. The cardiac septum 202 may be represented by a darker-blue/black mid ventricular line.

The activation map 210 may be obtained by combining electrocardiographic (ECG) and medical imaging data. This data may be stored in the memory 102. For example, the processing unit 110 may receive patient-specific data from the ECG system 104, the medical imaging system 106, and the 3D camera 108, or this data may be previously stored and retrieved from the memory 102. The processing unit 110 may determine the locations of the electrodes of the 12 lead ECG on the patient by applying electrocardiographic imaging (ECGI) method configured to determine the localization of the ECG within the heart tissue based on 12 lead ECG data. The ECG signals may be combined with a patient-specific 3D anatomical model of the heart and torso in order to compute the positions of cardiac isochrones.

The activation map 210 may include a localization point 212. As used herein, the term localization point may refer to an origin or exit site of an ECG beat within the heart tissue. For example, localization points may refer to an onset point of premature ventricular contraction (PVC) or an exit point of a VT beat. In particular, the localization point 212 of FIG. 2B corresponds to the starting point of a single PVC. FIG. 2B also shows the duration of the associated QRS complex, which for the illustrated example continued for 230 milliseconds. The localization point 212 is positioned on the epicardial surface of the heart myocardium. The scale provides the point of earliest activation (0 ms) and may be represented by a color, such as red. As the cardiac activation proceeds, the wave front may be identified as a progression of colors for the duration of the QRS waveform. Such a color representation may provide a map of the activation time sequence during the QRS complex.

Figure 3:
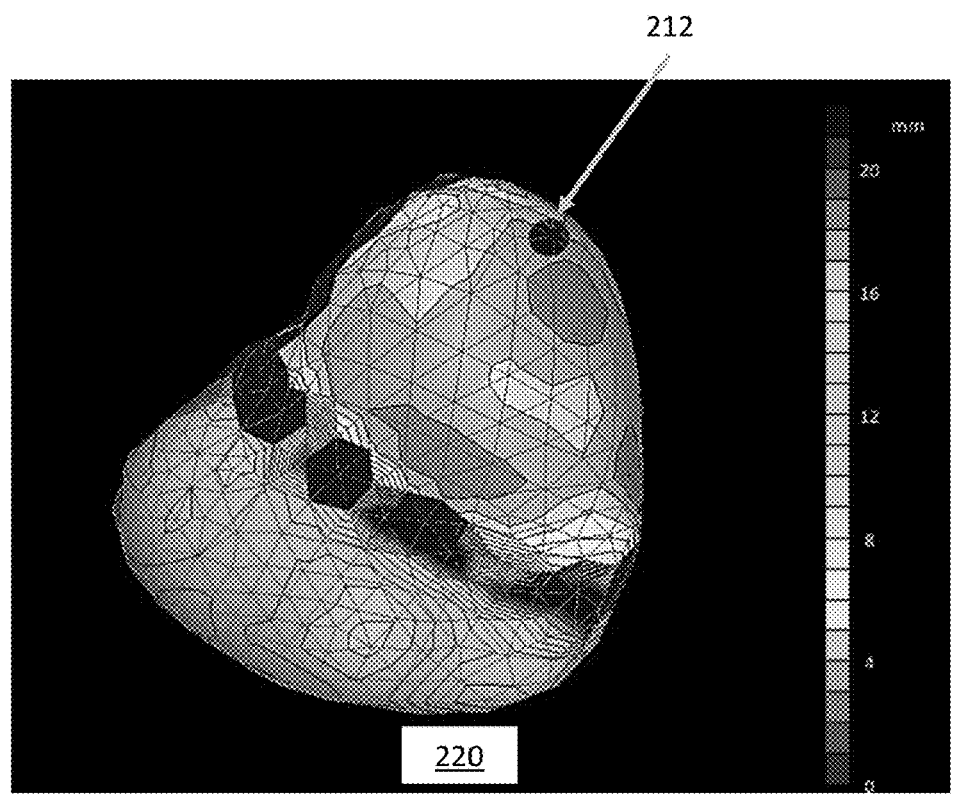
FIG. 3 shows a heart model that has been modified to include the localization point identified in the activation map according to various embodiments.

FIG. 3 shows a heart model 220 that has been modified to include the localization point 212 identified in the activation map 210. In particular, the localization point 212 may be superimposed on the patient specific 3D heart model 200 in order to form the modified heart model 220 including the myocardium's wall thickness. The heart model 220 may provide, for example, an accurate estimate of where and how much pressure should be applied to insert an ablation catheter within the ventricular myocardium in order to reach the localization point 212. This may assist in guiding an ablation catheter to the optimal therapy location. In the example illustrated in FIG. 3, the localization point 212 is identified on the endocardial surface of the right ventricle. Also, the right ventricle thickness is within the range of 3 mm to 6 mm, and the left ventricle is within the range of 8 mm to 14 mm. The localization point 212 is located within the basal lateral wall (i.e. closer to the valve plane) of the right ventricle.

Figure 4:
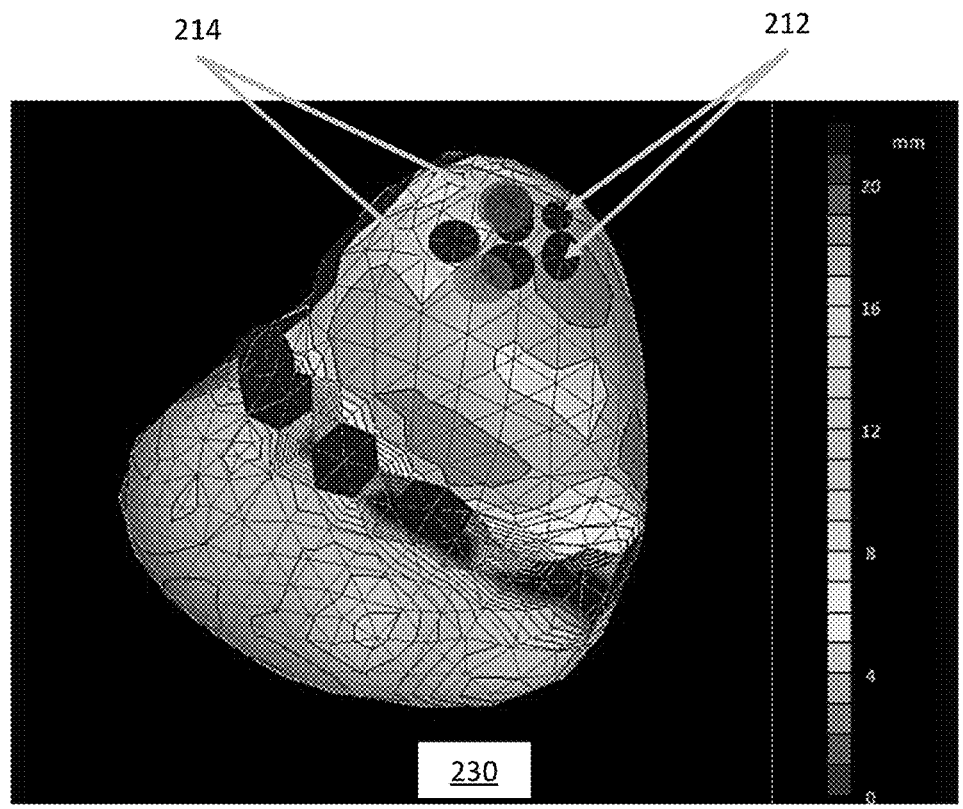
FIG. 4 shows a 3D heart model that has been modified to include multiple localization points according to various embodiments.

FIG. 4 shows a 3D heart model 230 that has been modified to include multiple localization points 212, 214. In particular, patients whose hearts have myocardial scaring (e.g., cardiomyopathy and/or ischemic heart disease) may also exhibit arrhythmias such as ventricular tachycardias. The analysis of multiple beats within these ventricular tachycardias may alternatively provide the exit point or points for the ventricular tachycardia reentrant loop and may lead to the location of the isthmus (true origin). In the heart model 230, five endocardial localization points 212 and two epicardial localization points 214 are identified. In this example, the localization points 212, 214 are located in the lateral region of right ventricle near the valve plane.

Figure 5:
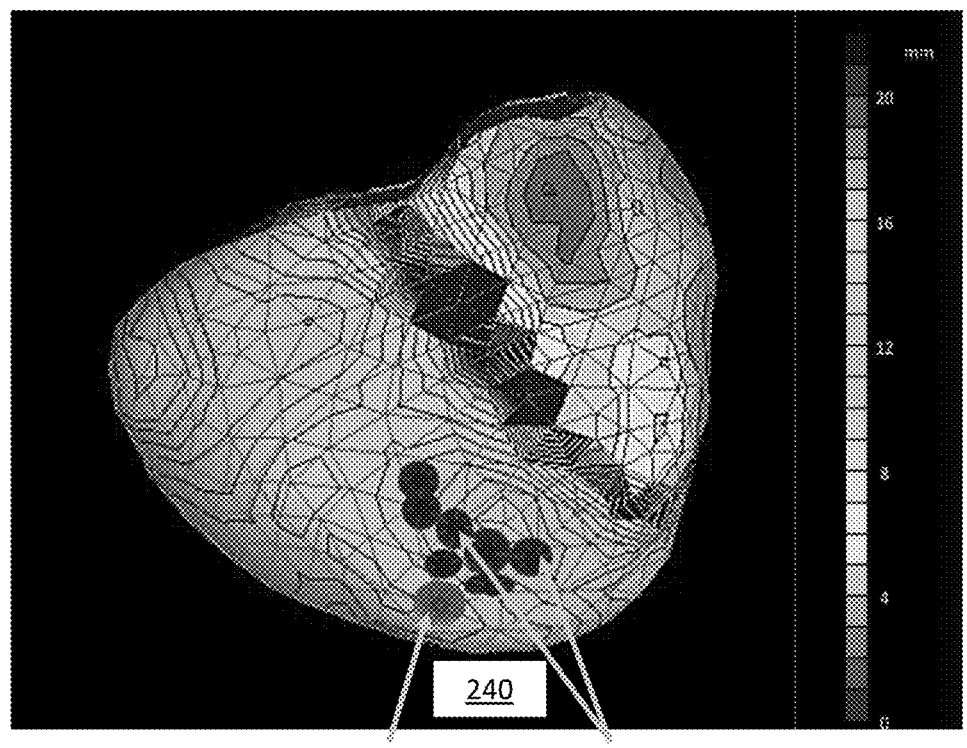
FIG. 5 shows a 3D heart model that has been modified to include seven endocardial surface localization points and one epicardial surface localization point, according to various embodiments.

FIG. 5 shows a 3D heart model 240 that has been modified to include seven endocardial surface localization points 212 and one epicardial surface localization point 214. Referring to FIG. 5, the localization points 212, 214 are disposed on the lateral region of the left ventricle, near the ventricular apex, which is indicative of exit points of corresponding VT beats.

Figure 6A:
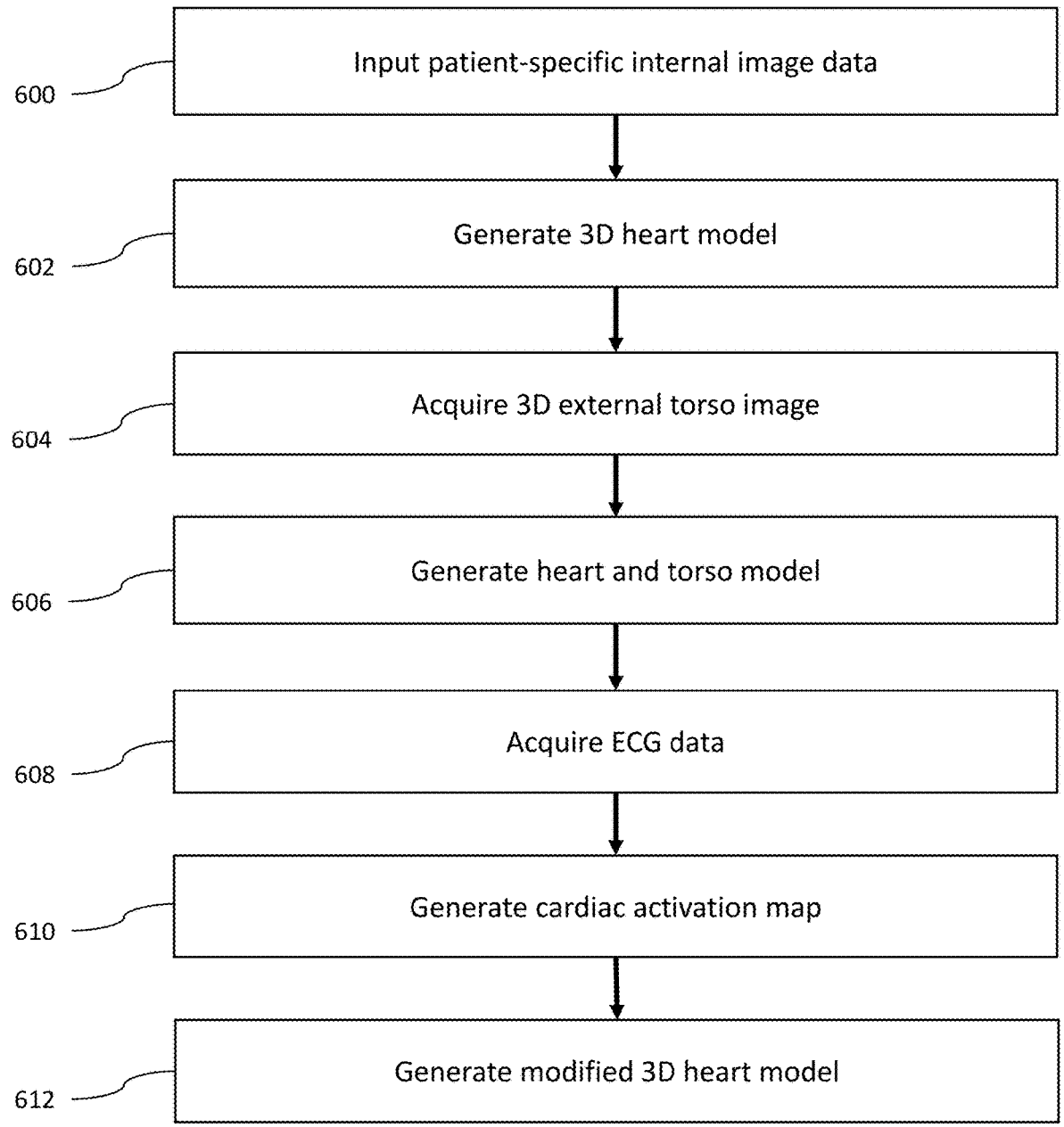
FIGS. 6A and 6B are flow diagrams illustrating the clinical operational workflow for a method of superimposing a PVC localization onto a patient-specific heart model according to various embodiments.
Figure 6B:
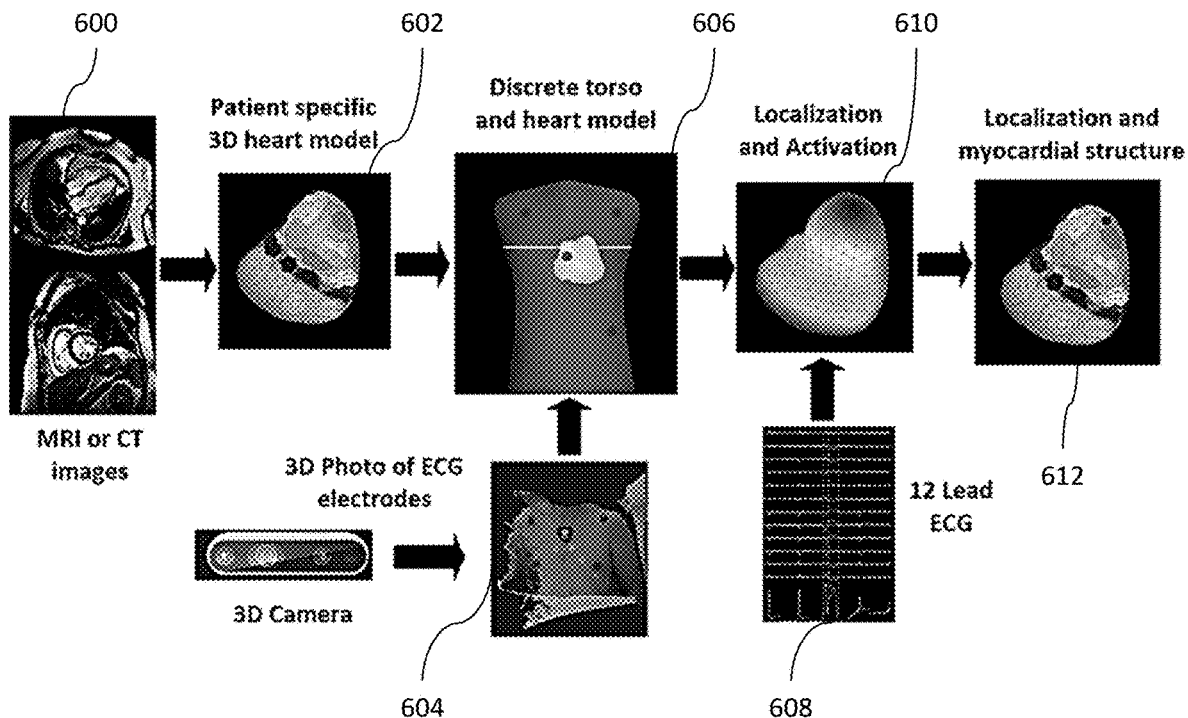

FIG. 6A is a process flow diagram illustrating operations of a method of generating superimposing a PVC localization onto a patient-specific heart model, according to various embodiments of the present disclosure. FIG. 6B is a flow diagram depicting the operations of the method illustrated in FIG. 6A. In particular, the method may be performed using the system 100 of FIG. 1.

Referring to FIGS. 1, 6A, and 6B, in operation 600, patient-specific internal image data, such as an MRI or CT scan of a patient, may be input to the system 100 as a 3D image. In operation 602, the 3D image may be aligned with a selected 3D heart model selected from a database to generate a patient-specific 3D heart model. A patient specific torso model may also be created in operation 602 using the MRI or CT scan data, and may include the heart model.

In operation 604, a 3D external image of the patient's torso may be taken. The image may include the locations of ECG electrodes used for a standard 12-lead electrocardiograph recording. The 3D external image may also include positioning patches used as anatomical reference markers during 3D image acquisition. In operation 606, the 3D external image may be merged with the 3D heart model, to generate a patient specific 3D heart and torso model, which may include identifying the locations of the ECG electrodes and alignment patches.

In operation 608, ECG data may be recorded using ECG electrodes positioned as shown in the 3D image and the torso and heart model. For example, a 12 lead ECG recording may be input to the system 100 with the recording including an arrhythmia, such as a PVC or VT.

In operation 610, a mathematical model (e.g., algorithm) may be applied to the ECG recording taken in operation 608 and using the electrode locations within the heart and torso model identified in operation 606. In particular, the algorithm may be applied to ECG data corresponding to one or more PVC beats, or one or more VT beats, in order to generate an inverse solution that may be used to calculate one or more localization points. A cardiac activation map may be generated based on the patient specific heart model created in operation 602 showing the propagation of electrical signals through the heart, including one or more localization points. For example, localization points may identify a PVC onset point or a VT entry or exit point.

In operation 612, the localization point or points may be applied to the 3D heart model formed in operation 602, in order to generate a modified 3D heart model that includes the localization point or points and cardiac wall thickness measurements. As such, one or more localization points may be presented simultaneously with corresponding myocardium thickness measurements, in the 3D heart model.

For example, for VT patients, operation 608 may include recording ECG data for multiple VT beats. For PVC patients, operation 608 may include recording ECG data for at least one PVC beat. As another example, operation 610 may include applying an algorithm to the ECG data corresponding to the VT beats, and generating a cardiac activation map including the exit points of each of the VT beats. The exit points may then be identified on the 3D heart model, such as shown in FIG. 4. The analysis results indicative of exit sites of the re-entrant loop may also be chronologically presented as endocardial sites 212 or epicardial sites 214, together with heart wall thickness measurements.

Figure 7:
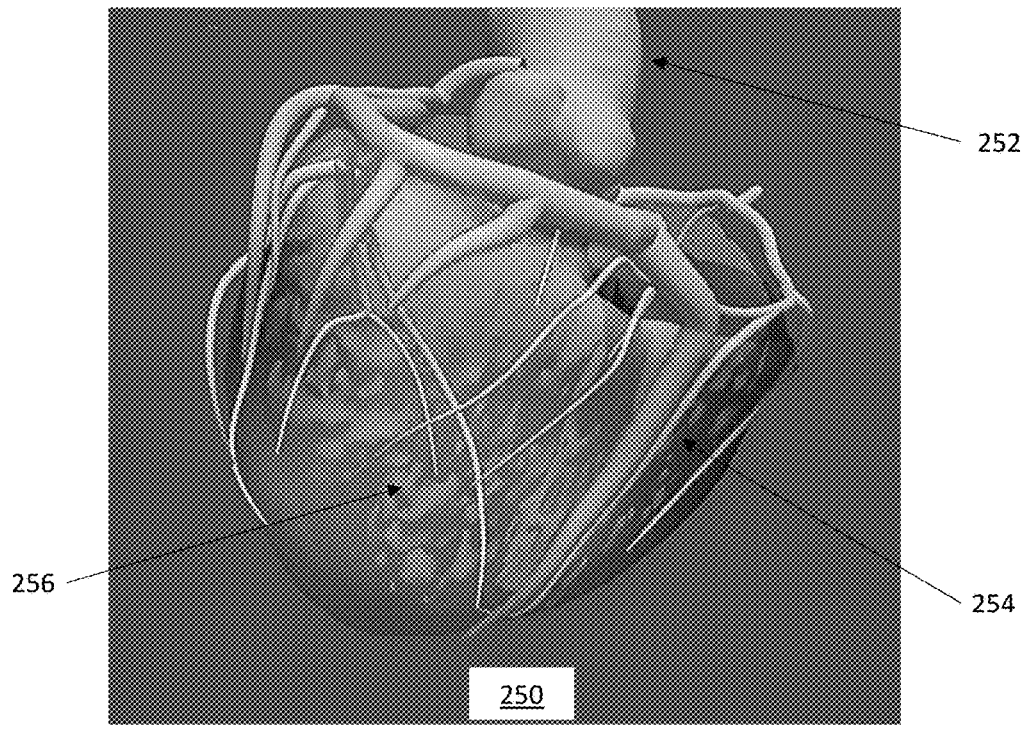
FIG. 7 shows a 3D heart model including additional anatomical features according to various embodiments.

In some embodiments, operation 602 may include identifying additional anatomical features in the 3D heart model. For example, as shown in FIG. 7, a 3D heart model 250 may additionally include features such as the aorta, aortic arch 252, coronary vascular structures 254 such as arteries and veins, scar tissue 256, or the like, to aid in the guidance of subsequent treatments, such as radio frequency (RF) ablation therapy, or the like.

Figure 8A:
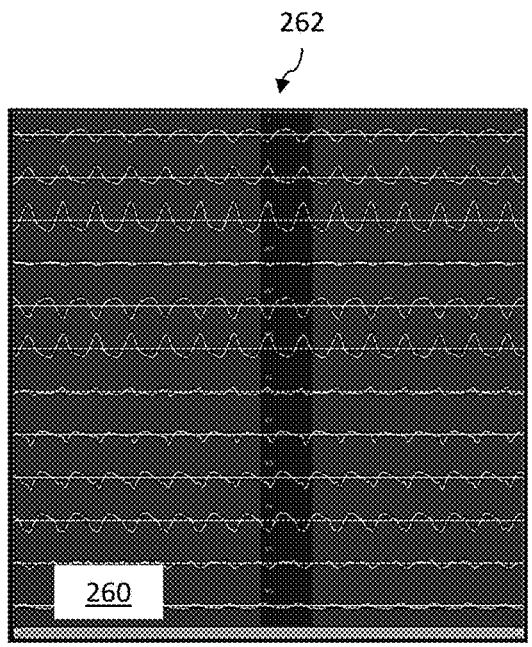
FIGS. 8A and 8B are screen shots showing a VT rhythm and a corresponding 3D heart model according to various embodiments.
Figure 8B:
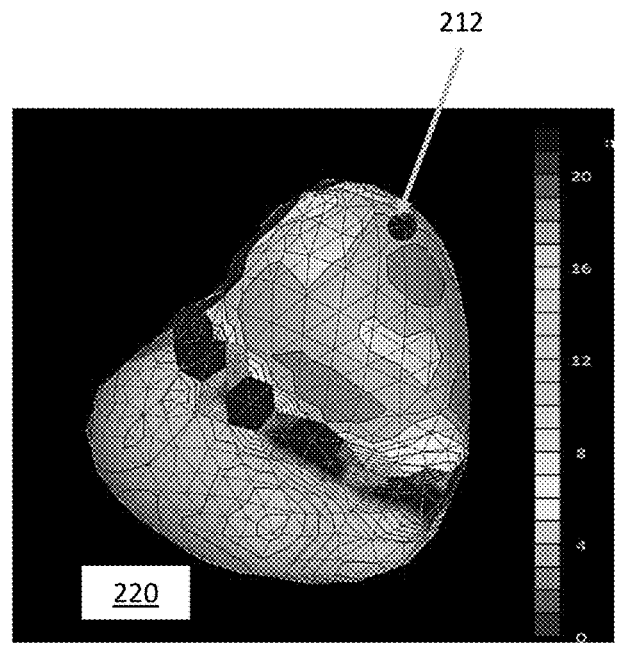
Figure 9A:
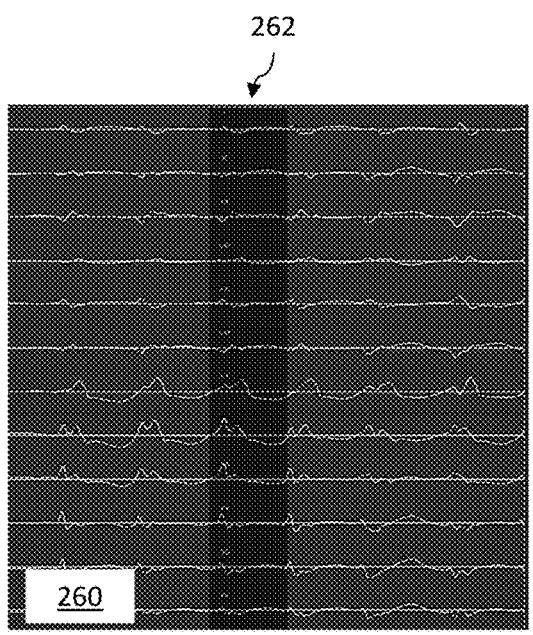
Figure 9B:
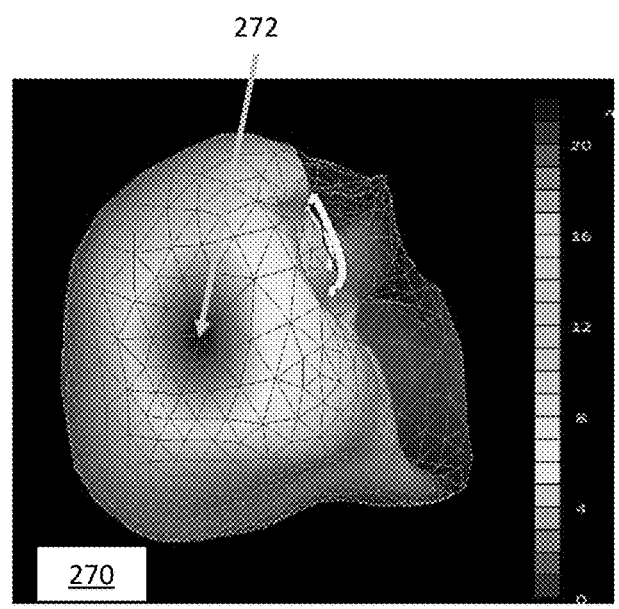
Figure 10A:
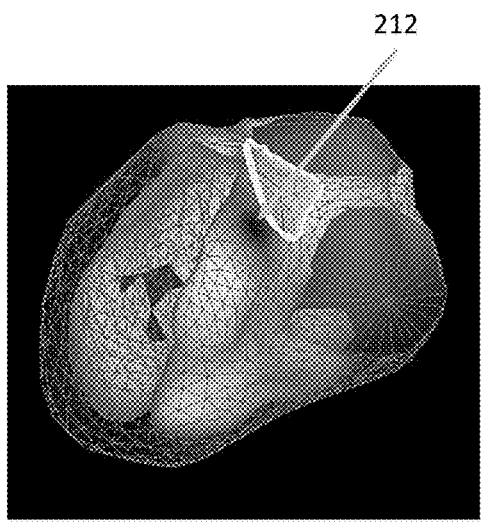
FIGS. 10A-10F are screen shots showing the location of VT exit sites for successive VT beats according to various embodiments.
Figure 10B:
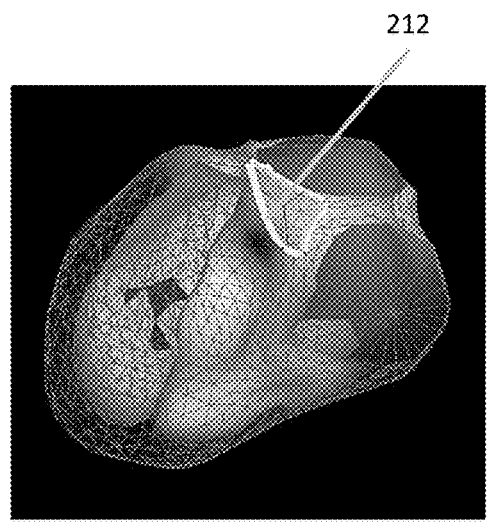
Figure 10C:
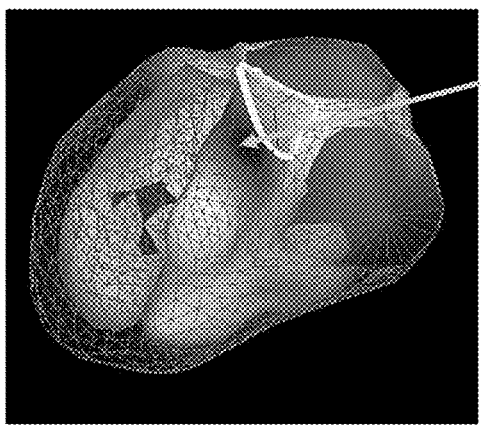
Figure 10D:
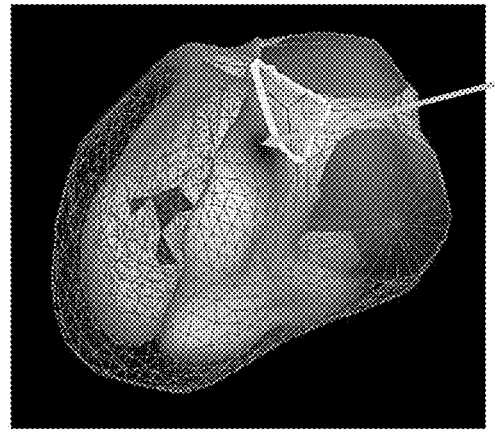
Figure 10E:
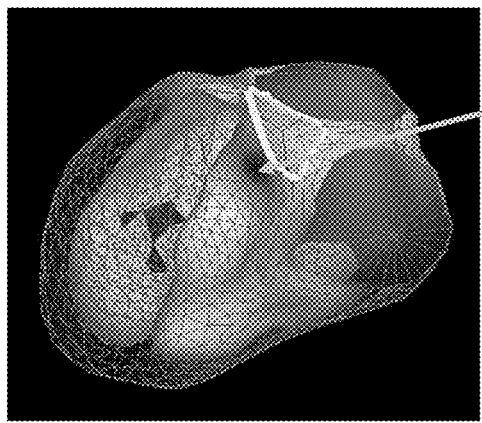
Figure 10F:
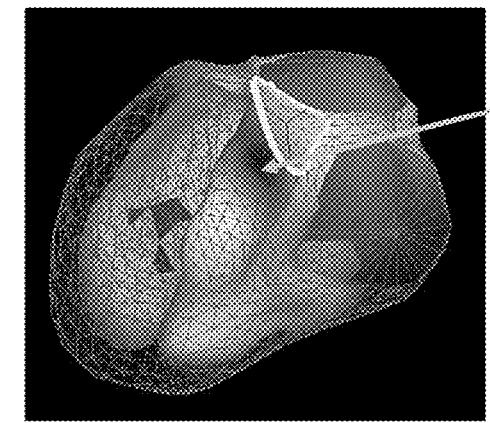

In various embodiments, a VT rhythm can also be displayed as individual beats in operation 612. For example, as shown in FIGS. 8A and 8B, a VT rhythm 260 may be displayed as a chronological sequence of individual ECG beats of the VT rhythm 260, which may be identified by a scrolling bar 262 that passes through each beat of an ECG display, while simultaneously displaying a 3D heart model 220 including corresponding localization points 212. This presentation may be based on analyzed clinical data. For example, as each ECG beat progresses through the VT rhythm, the next localization point may be displayed.

FIGS. 9A-9F are screen shots showing a VT rhythm and corresponding modified 3D heart models as successive localization points are displayed according to various embodiments. As shown in FIGS. 9A-9F, in alternative embodiments, a VT rhythm 260 and 3D heart model 270 may be displayed and dynamically modified in order to dynamically display exit sites 272 for each ECG beat of the VT rhythm 260, along with a corresponding activation map 270. In the example shown in FIGS. 9A and 9B, for the first ECG beat in the VT rhythm 260, the exit site 272 is located on the epicardial surface of the left ventricle of the heart.

In the example shown in FIGS. 9C and 9D, during the next ECG beat of the same VT rhythm 260, the exit site 272 shifts towards the ventricular apex and is on the endocardial surface of the left ventricle.

In the example shown in FIGS. 9E and 9F, during the next ECG beat of the same VT rhythm, the exit site 272 has shifted to the ventricular apex on the endocardial surface of the left ventricle.

By continuing to analyze each successive beat of the VT rhythm, the exit sites identified can provide an electrical representation and confirmation of the region of myocardial scar and provide an estimate of where to perform an RF ablation within the scar region. Additionally, if there are multiple beats with the same exit site identified, the exit sites may be presented as a density (or frequency) of these locations. In such embodiments, the multiple VT exit points may be displayed on the modified 3D heart model as a density distribution. For example, the density (or frequency) at each exit site, as shown in FIG. 5, may be presented as a bar graph with each location identified, or as a quantification near each exit site on the 3D heart model 240. Such a density distribution display presentation may also provide further insight into the location of the isthmus within the myocardium.

Patient case data from a patient with a normally structured heart and idiopathic ventricular tachycardia, should provide (with the absence of scar tissue) the analysis of the ECG beat with the localization of the origin for the ventricular arrhythmia An example of a patient case data with idiopathic ventricular tachycardia, the localization of 6 successive ECG beats results in the same localization point 212 with the data analysis results shown in FIGS. 10A-10F.

Many important advances have been made in the field of VT ablation; however, the identification of ablation target sites still relies on invasive electro-anatomical substrate mapping (i.e. patients with myocardial scar), which can be time-consuming and hindered by other factors. The non-invasive technology described herein can be used to guide the physician to the target area pre-procedurally to decrease the amount of time needed to search for the site.

The foregoing method descriptions and the process flow diagrams are provided merely as illustrative examples and are not intended to require or imply that the operations of the various embodiments must be performed in the order presented. As will be appreciated by one of skill in the art the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable medium or non-transitory processor-readable medium. The operations of a method or algorithm disclosed herein may be embodied in a processor-executable software module and/or processor-executable instructions, which may reside on a non-transitory computer-readable or non-transitory processor-readable storage medium. Non-transitory server-readable, computer-readable or processor-readable storage media may be any storage media that may be accessed by a computer or a processor. By way of example but not limitation, such non-transitory server-readable, computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory server-readable, computer-readable and processor-readable media. Additionally, the operations of a method or algorithm may reside as one or any combination or set of codes and/or instructions on a non-transitory server-readable, processor-readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the claims. Thus, the present invention is not intended to be limited to the embodiments shown herein but is to be accorded the widest scope consistent with the following claims and the principles and novel features disclosed herein.

What is claimed is:

1. A method of generating a modified 3D heart model with arrhythmia localization, comprising:

generating image data of a heart of a patient using a magnetic resonance imaging (MRI) device or a computed tomography (CT) imaging device;

generating by a processing unit coupled to a memory a three-dimensional (3D) heart model of the heart using the image data, the 3D heart model comprising myocardium wall thickness measurements of the heart derived from the image data;

capturing using a 3D camera a 3D image of the patient's torso including the location of ECG electrodes on the patient used to collect electrocardiogram (ECG) data;

merging by the processing unit the 3D image of the patient's torso with the 3D heart model to form a torso and heart model comprising positions of the ECG electrodes relative to the heart model based on the location of the ECG electrodes in the 3D image;

generating by the processing unit an activation map of the heart by combining ECG data, recorded using the ECG electrodes during ventricular tachycardia (VT) of the heart, with the heart and torso model providing the positions of the ECG electrodes;

performing by the processing unit an inverse solution calculation, using the ECG data recorded during VT and the positions of the ECG electrodes in the heart and torso model, to identify a VT exit point on the activation map;

modifying by the processing unit the 3D heart model to include the VT exit point identified on the activation map; and delivering, based on the VT exit point identified in the modified 3D heart model, ablation therapy to the identified VT exit point location to treat the ventricular tachycardia.

2. The method of claim 1, wherein generating by the processing unit a 3D heart model further comprises:

selecting by the processing unit a cardiac 3D reference model stored in the memory based on the image data; and adjusting by the processing unit the 3D reference model based on image data.

3. The method of claim 1, wherein the VT exit point includes an indication as to whether the VT exit point is located on an endocardial surface or an epicardial surface of the modified 3D heart model.

4. The method of claim 1, wherein the modified 3D heart model comprises at least one heart structure selected from an aorta, an aortic arch, coronary vascular structures, pulmonary vascular structures, or heart scar tissue indicative of ischemic heart disease.

5. The method of claim 1, wherein:
the activation map comprises multiple VT exit points; and
modifying by the processing unit the 3D heart model comprises modifying the 3D heart model to include the multiple VT exit points.

6. The method of claim 5, wherein the multiple VT exit points are displayed by the processing unit on the modified 3D heart model as a density distribution.

7. A medical system that provides arrhythmia localization and model merging, comprising:
a memory;
a 3D camera; and
a processing unit coupled to the memory and the 3D camera and configured with processor-executable instructions to perform the method of claim 1.

* * * * *